United States Patent [19]

Kumagai et al.

[11] Patent Number: 5,620,709
[45] Date of Patent: Apr. 15, 1997

[54] CALCIUM CONTAINING COMPOSITION FROM SEA URCHIN WITH HIGH ORAL BIOAVAILABILITY

[75] Inventors: Yoshinari Kumagai, Fujisawa; Azuma Kubo, Hirakata, both of Japan

[73] Assignee: Kabushiki Kaisha Megawave Japan, Tokyo, Japan

[21] Appl. No.: 274,867

[22] Filed: Jul. 14, 1994

[30] Foreign Application Priority Data

Jul. 16, 1993 [JP] Japan .................................. 5-176503
Apr. 21, 1994 [JP] Japan .................................. 6-083516
Apr. 28, 1994 [JP] Japan .................................. 6-091694

[51] Int. Cl.$^6$ .......................... A61K 33/06; A61K 33/00
[52] U.S. Cl. .......................................... 424/682; 424/600
[58] Field of Search ................................. 424/682, 686, 424/687, 600

[56] References Cited

PUBLICATIONS

Abstract of JP5161480, published Jun. 29, 1993.
Abstract of JP58036348, published Mar. 3, 1983.
Abstract of JP55081552, published Jun. 19, 1980.
Abstract of JP53038593, publication date Apr. 8, 1978.
Abstract of JP3236750, publication date Oct. 22, 1991.

*Primary Examiner*—Theodore J. Criares
*Attorney, Agent, or Firm*—Fish & Richardson PC

[57] ABSTRACT

A calcium containing composition was obtained by baking sea urchin shells. This calcium containing composition gives superior oral bioavailability, has better appearance and taste, contains low impurity, and provides high yield. Therefore, this sea urchin shell derived calcium containing composition is useful in the treatment and prophylaxis of various diseases which require calcium supplementation such as hypocalcemia, osteoporosis, renal osteodystrophy, and so forth. Also, it is suitable to combining into health food and feed for the purpose of calcium supply.

5 Claims, 1 Drawing Sheet

5,620,709

CALCIUM CONTAINING COMPOSITION FROM SEA URCHIN WITH HIGH ORAL BIOAVAILABILITY

BACKGROUND OF THE INVENTION

1. Field of the Invention

This invention is related to a calcium containing composition derived from the shell of sea urchin which gives high oral bioavailability, manufacturing method of such a composition, food containing such a composition, feed containing such a composition, and pharmaceutical compositions containing such a composition.

2. Description of the Related Art

Various types of calcium formulations and health food which contain calcium as an active component have been proposed to supplement dietary calcium thus far. The calcium used for such formulation and health food is generally made from calcium carbonate derived from mineral origin such as limestone and lime milk, calcium phosphate, calcium hydroxide, calcium lactate, calcium gluconate, shellfish derive calcium such as oyster shells, other mollusks shells and corals, crustaceans such as crabs, and shrimps, seaweeds such as tangles, hijikia, and undaria, mammalian bones, egg shells, and so forth.

However, the calcium made from these materials generally does not give sufficient oral bioavailability. Furthermore, oral bioavailability of calcium in human is generally extremely low unless it is administrated with Vitamin D or proteins and it is difficult to supply the required amount of calcium to human by itself. In addition, people in Japan take only 531 mg per day of calcium in average according to the National Nutrition Investigation Report by the Ministry of Health and Welfare. This level is less than a half of that in the Western countries.

Under such circumstances, the inventors herein have tried to find a calcium containing composition with high oral bioavailability. As a result, the invention herein was achieved by discovering that a calcium containing composition with high oral bioavailability can be obtained, to our astonishment, by baking sea urchin shells which have been disposed without any use.

SUMMARY OF THE INVENTION

This invention herein is to provide a calcium containing composition derived from sea urchin shells. Also, this invention includes the manufacturing method of such a composition, foods containing such a composition, and pharmaceutical compositions containing such a composition. This is no limitation about the species of the material sea urchin, e.g.; "Bafun-uni" (Hemicentrotus pulcherrimus), "Murasaki-uni" (Anthocidaris crassispina), "Ezobafun-uni" (Strongylocentrotus intermedius), "Aka-uni" (Pseudocentrotus depressus), etc. can be used. To manufacture the calcium containing composition described in this invention, the soft content held in the sea urchin shells shall be removed initially. This can be done, for example, by crashing sea urchins and removing their ovary and meat held in the shells. The shells are washed after the removal of contents. Such washing process can be done with water.

Then, the shells are to be baked at high temperature. The baking temperature is preferably 500° to 1500° C. The baking time is preferably 0.5 to 1.5 hours. For example, it is be heated at 1000° C. for 1 hour when a baking oven is used, or at 800° C. for 1 hour when a vacuum oven is used. By such heating, calcium in the sea urchin shells as calcium carbonate ($CaCO_3$) is converted to calcium oxide (CaO). After baking, such CaO can be converted, if necessary, into any useful formulation such as calcium carbonate, calcium hydroxide, calcium citrate, calcium alginate, etc. For example, conversion to calcium carbonate can be done by giving carbon dioxide ($CO_2$) to the calcium oxide. In the meantime, there should not be any problem about toxicity as this calcium derived from sea urchin shells is obtained from an edible raw material.

Furthermore, food, animal feed, or pharmaceutical composition containing this calcium containing composition derived from heated sea urchin shell in this invention can be made by, for example, mixing this calcium containing composition derived from baked sea urchin shells with citric acid and other formulation agents in common manners to form tablets or granules, or otherwise, dissolving with other flavors to formulate for drinking use. The content of the calcium containing composition can be properly determined, but it is usually 10 to 50 weight % of total amount of food, etc. In this manner, high oral bioavailability of calcium can be achieved by taking the food, etc. containing this calcium derived from sea urchin shell in this invention. The above and other objects, features and advantages of the present invention will become clear from the following description of the preferred embodiment thereof, taken in conjunction with the accompanying drawings.

BRIEF DESCRIPTION OF THE DRAWINGS

The FIG. 1 herein indicates the serum calcium level when various calcium containing compositions were orally administrated to the parathyroidectomized rats (Serum calcium concentration 24 hours after the first administration of the samples was set 100 and the relative value at every 24 hours thereafter in each group was indicated. In the meantime, it was confirmed that serum calcium level 24 hours after the first administration of the sample was as low as the level directly before the first administration.).

DESCRIPTION OF THE PREFERRED EMBODIMENTS

Example 1

Figure 1:
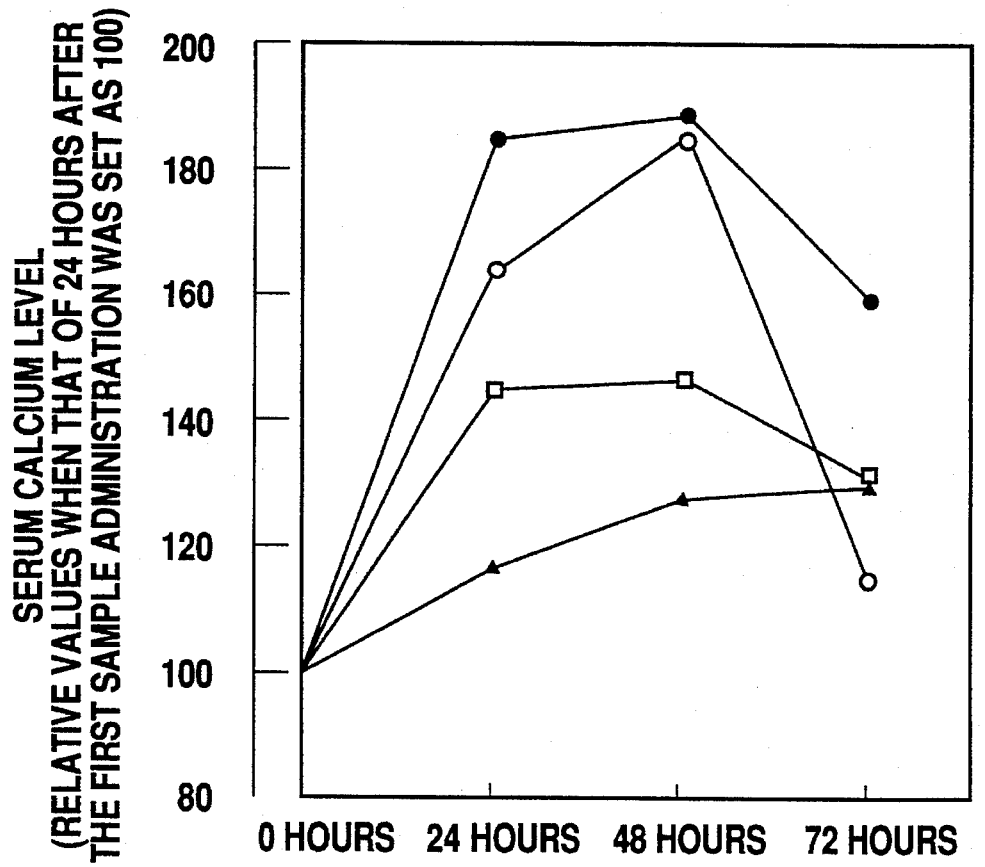

"Bafun-uni" (Hemicentrotus pulcherrimus) and "Murasaki-uni" (Anthocidaris crassispina) were washed with water after the mean portion was removed with a spatula. These sea urchin shells were baked at 1000° C. for 1 hour in a oven. By such heating, the calcium contained as calcium carbonate in the sea urchin shells was converted into the form of calcium oxide. After heating, an appropriate amount of water was added, mixing to react to form calcium hydroxide. The Table 1 indicates the result of the quantitation of each component.

TABLE I

Analytical Data of Sea Urchin Shell-Derived Calcium Containing Composition

| Components | Quantity | Analytical Methods |
| --- | --- | --- |
| Phosphorus | 101 mg/100 g | Vanadato molybdate Spectrophotometry |
| Iron | 6.03 mg/100 g | Low phenanthroline Absorption Spectrophotometry |
| Calcium | 52.2% | Potassium Permanganate Titration |

TABLE I-continued

Analytical Data of Sea Urchin Shell-Derived Calcium Containing Composition

| Components | Quantity | Analytical Methods |
|---|---|---|
| Sodium | 665 mg/100 g | Atomic Absorption Spectrometry |
| Potassium | 130 mg/100 g | Atomic Absorption Spectrometry |
| Magnesium | 2.14% | Atomic Absorption Spectrometry |
| Chlorine | 0.18% | Volhard's Method |
| Arsenic (as $A_{s2}O_3$) | Not Detected (<0.55 pm) | DDTC-Ag Absorption Spectrophotometry |
| Heavy Metals (as Pb) | 2.3 ppm | Sodium Sulfide Colorimetry |
| Copper | 2.1 ppm | Atomic Absorption Spectrometry |
| Zinc | 34.2 ppm | Atomic Absorption Spectrometry |
| Manganese | 1.5 ppm | Atomic Absorption Spectrometry |
| Sulfur | 0.05% | Barium Sulfate Gravimetry |

Then, the characteristics of the calcium containing composition of this invention was compared to the calcium containing compositions made from other raw materials. The comparison of the samples were done after the calcium included as calcium carbonate, etc. in each raw material was once converted into the form of calcium oxide by heating at 1000° C. for 1 hour, then was again converted into the form of calcium carbonate by adding carbon dioxide gas to make it edible. The result is indicated by Table 2.

TABLE 2

Comparison of Characteristics of Various Calcium Containing Compositions

| Raw Materials | Appearance | Taste | Impurity | Yield (%) |
|---|---|---|---|---|
| Sea Urchin Shells | Pure White | Very Mild | No | 65 |
| Oyster Shells | Pale Gray | Stimulative | Yes | 35 |
| Scallop Shells | Pale Yellow | Stimulative | Yes | 40 |
| Coral | White and Hard | Stimulative | Yes | 40 |
| Egg Shells | Pale yellow | stimulative | No | 45 |

As indicated by Table 2, the calcium containing composition derived from sea urchin shells provides preferable appearance and taste, does not contain impurity and give high yield.

Comparison of oral bioavailability was also conducted between the calcium containing composition derived from sea urchin shells of this invention and other types of calcium containing compositions derived from other raw materials.

Positive control samples used in this experiment were sedimented calcium carbonate 6th Edition of Japanese Pharmacopeia which is used as therapeutic agent with more than 98.5% purity, calcium lactate, and calcium chloride (12th Revision of Japanese Pharmacopeia).

Rat intestine was used for testing bioavailability.

Namely, rats were divided into the groups of five animals, anesthetized, opened the abdomens, occluded the intestines, and then blood was sampled from the intestinal vein. After that, 5 ml of aqueous solutions of 2% sedimented calcium carbonate, 2% calcium lactate, 2% calcium chloride, and 2% sea urchin shell derived calcium of this invention respectively at pH 2.0 were injected into the intestine. After injection, blood was sampled from intestinal vein every 10 minutes, and the total serum calcium ion concentration was measured.

When 5 ml of aqueous solution of 2% sea urchin shell-derived calcium containing composition at pH 2.0 was injected into the intestine, serum calcium level started to increase 10 minutes later, and significant increase was observed 30 minutes later. To our surprise, the level of serum calcium ion induced by sea urchin shell derived calcium containing composition 8.5 times higher than that by sedimented calcium carbonate, 4 times higher than that by calcium chloride, and 3 times higher than that by calcium lactate.

Example 2

The calcium containing composition derived from sea urchin shells in this invention was administrated to parathyroidectomized rats to compare oral bioavailability of this composition to that of other form of calcium containing composition. In the meantime, "Sea urchin shell derived calcium containing composition" and "Oyster shell derived calcium containing composition" used here are the identical to those used in Example 1. Parathyroidectomy was performed with several rats and low calcium diet (Normal rat diet containing only 0.1% of calcium) was given for 156 hours to lower the blood calcium level. Twenty-four healthy rats (12 each of males and females) with sufficiently low blood calcium level were selected and divided into four groups of 6 animals (the same number of males and females in one group, respectively). These animals were fasted then, and the first administration of the samples were done 12 hours thereafter.

The following treatment was done for respective groups after that.

The following treatment was done for respective groups after that.

1) Negative Control Group: Saline (2 ml) injected into stomach as the first sample administration. Low calcium diet was given from 24 to 96 hours after that.

2) Positive Control Group: Saline (2 ml) solution of calcium carbonate (68.4 mg of calcium/kg rat weight was dissolved into the saline) was injected into stomach as the first sample administration. Low calcium diet mentioned above containing calcium carbonate (68.4 mg calcium/kg rat weight per day was mixed in the diet) was given from 24 to 96 hours after that.

3) Sea Urchin Shell Derived Calcium Group: Saline solution (2 ml) of the sea urchin shell derived calcium containing composition (68.4 mg of calcium/kg rat weight was dissolved into the saline) was injected into stomach as the first sample administration. Low calcium diet mentioned above containing the sea urchin shell derived calcium containing composition (68.4 mg calcium/kg rat weight per day was mixed in the diet) was given from 24 to 96 hours after that.

4) Oyster Shell Derived Calcium Group: Saline solution (2 ml) of the oyster shell derived calcium containing (68.4 mg of calcium/kg rat weight was dissolved into the saline) was injected into stomach as the first sample administration. Low calcium diet mentioned above containing the oyster shell derived calcium containing composition (68.4 mg calcium/kg rat at weight per day was mixed in the diet) was given from 24 to 96 hours after that.

Low calcium diet was provided to all four groups above between 6 and 24 hours after the first sample administration.

Blood was drawn all animals of the above 4 groups immediately before the first sample administration (0 hour), and at 24, 48, 72, and 96 hours thereafter, and serum calcium level was measured. The result was indicated in FIG. 1 (24 hours after the first sample administration is set as 0 hour in this Figure. However, it was affirmed that the serum calcium level at 24 hours after the first sample administration came down to the same level as that at 0 hour.). As indicated by this Figure, the increase of serum calcium level was higher in the order of sea urchin shell derived calcium group>oyster shell derived calcium group>positive control group>negative control group, and it was demonstrated that the sea urchin shell derived calcium containing composition is superior in oral bioavailability.

Feces of all rats in all 4 groups were collected between the first sample administration and 24 hours thereafter and the calcium content was quantified. The result is shown in the Table 3.

TABLE 3

Fecal Calcium Excretion When Various Calcium
Containing Composition were Orally Administered
to the Parathyroidectomized Rat

|  | Fecal Calcium Content (mg) |
| --- | --- |
| Negative Control | 0.881 |
| Positive Control | 1.624 |
| Sea Urchin Shell Derived Calcium | 0.475 |
| Oyster Shell Derived Calcium | 1.025 |

As indicated in this table, fecal calcium excretion was higher in the order of Positive Control>Oyster Shell Derived Calcium>Negative Control>Sea Urchin Shell Derived Calcium. The fact that fecal calcium excretion was lowest in Sea Urchin Shell Derived Calcium Group means that sea urchin shell derived calcium containing composition is absorbed from intestine better when it is orally administrated and excreted less into feces. Namely, it Was confirmed that sea urchin shell derived calcium containing composition is superior in bioavailability compared to other form of calcium containing composition when they are orally administrated. In general, the dietary passage time in rat is said to be about 6 hours. Therefore, each sample injected into stomach with saline at the first sample administration is regarded to be excreted to the feces during first 24 hours time period unless it is not administrated at intestine.

Normal rats and parathyroidectomized rats with lower serum calcium level were used in the Examples 1 and 2, respectively. However, both examples demonstrate the superior oral calcium bioavailability of sea urchin shell derived calcium containing composition quantitatively. By these facts, it is evident that the urchin shell derived calcium containing composition of this invention is useful in the treatment prophylaxis of various diseases which require calcium supplementation such as hypocalcemia, osteoporosis, renal osteodystrophy, and so forth. Furthermore, taking the fact into consideration that the sea urchin shell derived calcium containing composition has better appearance and taste and contains low level of impurity, as indicated in Example 1, it is evident that this composition is extremely suitable to combining into health food and animal feed for the purpose of calcium supply.

This invention provided a calcium containing composition which is superior in oral bioavailability, has better taste, contains low impurity, and gives high yield from sea urchin shells that used to be disposed.

Such sea urchin shell derived calcium containing composition is useful in treatment or prophylaxis of disease which require calcium supplementation such as hypocalcemia, osteoporosis, and renal osteodystrophy. Also, it is suitable to combining into health food and animal feed for the purpose of calcium supply.

While there has been shown what is considered to be the preferred embodiment of the invention, it will be manifest that many changes and modifications may be made therein without departing from the essential spirit of the invention. It is intended, therefor, in the annexed claims, to cover all such changes and modifications as may fall within the true scope of the invention.

We claim:

1. A calcium-containing composition comprising calcium, which calcium is obtained by (1) providing sea urchin shells, and (2) heating the shells at a temperature not greater than 1500° C. so as to form a calcium-containing composition, and which calcium has an oral bioavailability, measured in terms of urinary calcium excretion and/or fecal calcium excretion in rate over a time period of 0–48 hours, superior to the oral bioavailability of an equal amount of calcium produced by heating oyster shells.

2. The composition according to claim 1, wherein the composition is in the form of a food product.

3. The composition according to claim 1, wherein the composition is in the form of an animal feed supplement.

4. The composition according to claim 1, wherein the composition is in a medicine in an effective amount for treating a disease selected from the group consisting of hypocalcemia, osteoporosis, and renal osteodystrophy.

5. The composition according to claim 1, wherein the composition is in the form of a calcium supplement.

* * * * *

UNITED STATES PATENT AND TRADEMARK OFFICE
CERTIFICATE OF CORRECTION

PATENT NO. : 5,620,709

DATED : April 15, 1997

INVENTOR(S) : Yoshinari KUMAGAI, Azuma KUBO

It is certified that error appears in the above-identified patent and that said Letters Patent is hereby corrected as shown below:

On the title page, item [73]:

Please change Assignee from "Kabushiki Kaisha Megawave Japan, Tokyo, Japan" to --Big Bear Bio, Inc. Foster City, California--.

Signed and Sealed this

Second Day of December, 1997

*Attest:*

BRUCE LEHMAN

*Attesting Officer*   Commissioner of Patents and Trademarks